(12) United States Patent
Eastland

(10) Patent No.: US 11,558,124 B1
(45) Date of Patent: Jan. 17, 2023

(54) METHODS FOR HELICAL WAVE ENCODING

(71) Applicant: The United States of America as represented by the Secretary of the Navy, Keyport, WA (US)

(72) Inventor: Grant Eastland, Bremerton, WA (US)

(73) Assignee: The United States of America as represented by the Secretary of the Navy, Keyport, WA (US)

( * ) Notice: Subject to any disclaimer, the term of this patent is extended or adjusted under 35 U.S.C. 154(b) by 328 days.

(21) Appl. No.: 16/873,828

(22) Filed: Jul. 17, 2020

Related U.S. Application Data

(60) Provisional application No. 62/973,005, filed on Sep. 10, 2019.

(51) Int. Cl.
*H04B 11/00* (2006.01)
*A61B 5/00* (2006.01)

(52) U.S. Cl.
CPC ............ *H04B 11/00* (2013.01); *A61B 5/0015* (2013.01)

(58) Field of Classification Search
CPC ....... H04B 11/00; A61B 5/0015; G03B 17/08; G02B 23/22
See application file for complete search history.

(56) References Cited

U.S. PATENT DOCUMENTS

| | | | |
|---|---|---|---|
| 3,715,674 A * | 2/1973 | Bahr | H03H 9/14597 331/107 A |
| 2012/0212375 A1 * | 8/2012 | Depree, IV | H01Q 15/0086 977/762 |
| 2016/0198954 A1 * | 7/2016 | Wang | A61B 5/0095 600/407 |
| 2019/0007145 A1 * | 1/2019 | Morozov | H04B 11/00 |
| 2020/0345873 A1 * | 11/2020 | Ashrafi | A61L 2/12 |

* cited by examiner

*Primary Examiner* — Daniel L Murphy
*Assistant Examiner* — Amie M Ndure
(74) *Attorney, Agent, or Firm* — Stephen J. Leahu; Naval Undersea Warfare Center

(57) ABSTRACT

A communication system utilizes acoustic helical waves to transmit and receive information. The acoustic communication system can communicate securely underwater or in fluids and may be used to communicate with underwater vehicles or in medical settings.

10 Claims, 9 Drawing Sheets

Right-handed

Left-handed

METHODS FOR HELICAL WAVE ENCODING

CROSS REFERENCE TO OTHER PATENT APPLICATIONS

The present application claims the benefit of U.S. provisional patent application 62/973,005 filed Sep. 10, 2019 and titled: Helical Wave Encoding, the complete disclosure of which is incorporated herein by reference.

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Transmitting information securely presents several challenges. These challenges are compounded when communicating underwater or in liquid mediums since the ability to communicate via electromagnetic means such as, for example, radio or light waves is limited to non-existent. Communication in water or other liquids therefore has traditionally employed acoustic methods which transmit information by sending and receiving a pressure wave encoded, or modulated, with information.

FIG. 1 shows a prior art communication system in which a first device 1 encodes a message to be transmitted by an acoustic communications modem 2. Acoustic communications modem 2 then transmits an encoded pressure wave 4, which is received at a hydrophone 5 which includes a second acoustic communications modem 6. The received encoded pressure wave 4 is then demodulated, or decrypted by a second device 8, and the information output to an end user, device, or other recipient.

Prior art communication networks of the type illustrated in FIG. 1 use a variety of methods to modulate, or encode, information onto the pressure wave. Most such prior art methods utilize modulation techniques analogous to those used in radio transmissions to encode information. A first of these methods works similar to FM radio and encodes information by modulating the frequency of the pressure wave. A second of these methods works similar to AM radio and encodes information by modulating the amplitude or strength of the pressure wave to encode the information.

The physics and operation of prior art underwater and acoustic communications channels introduce numerous limitations and challenges into the operation of such communication systems. First, when the receiver and the transmitter are in motion relative to each other, Doppler effects can introduce time and frequency changes into the message—in much the same way a police siren changes pitch as it approaches and then passes by. These Doppler effects pose difficulties in demodulating or extracting information from the transmitted pressure wave.

Second, the transmitted prior art pressure waves can be subject to other forms of interference such as, for example, multipath interference. FIG. 2A, diagrams one type of multipath distortion in which one portion 80 of the transmitted pressure wave 79 bounces off an object, such as rock 82 in the transmission path. Receiver 84 thus receives reflected signal 80 at a different time then wave 79 resulting in distortion.

Alternatively, as shown in FIG. 2B, as the transmitted pressure wave 79 travels through the water or liquid, wave 79 may transit through regions where the density of the water or liquid changes. These changes in density naturally occur as a function of thermal gradients or changes in the height of the column of water. When the density of the liquid or water changes, the speed at which the pressure wave travels also changes. Thus, one faster moving portion 86 of the pressure wave, can 'catch up to' an earlier transmitted portion 88. This situation also causes interference 90 and compromises the ability to detect and accurately demodulate prior art communications signals. In the worst case scenario shown in FIG. 2B, the overtaking wave 8G is out of phase with the slower moving wave 88 causing the sum of the two waves 90 to equal a complete loss of signal.

Third, the characteristics of the fluid medium constrain the distance over which a message can be reliably sent. Higher frequency sounds are heavily damped in water and cannot be sent reliably over distance. For this reason, lower frequency sounds are typically used for acoustic underwater communication. Lower frequency pressure waves, however, require more time to transmit the same amount of information as higher frequency waves. Operators and designers must therefore continually tradeoff between the long distance communication afforded by lower frequencies and the higher capacity, shorter timeline communications afforded by higher frequencies.

Recently, prior art electromagnetic frequency communications methods began to include an additional type of modulation: a helical wave which corkscrews about an imaginary access as it propagates. For example, a left turning corkscrew can be used to indicate a first type of information, while a right turning corkscrew can be used to indicate a second type of information. Existing prior art methods, however, require the operator or the system to interrupt or stop transmission of a message to change the helicity of the wave. This fact increases the time needed to transmit any given message. This fact also increases the complexity of any communication system employing this method, since a means or methodology for interrupting the signal, and then changing the helicity of the wave are both required. In existing systems, this step of interrupting the signal, consists of switching between discrete devices: each dedicated to transmitting waves of a specific helicity. In prior art systems, this step of switching between devices is sometimes even performed manually.

Prior art helical wave methods and apparatus are therefore especially unsuited for underwater communications due to their architectures and operating characteristics as described above. The complexity of prior art helical wave methods increases production costs, decreases reliability, and increases the number and frequency of maintenance tasks. Each of these attributes makes prior art spiral encoding methods unsuitable for use in the harsh environment of undersea communications. Any requirement for manual intervention to switch the helicity of the wave makes prior art radio and light helical wave systems unusable undersea or other hostile environments, around sensitive equipment, in tight quarters, or in certain medical applications. Prior art helical radio and light methods are electromagnetic waves and therefore also do not describe or anticipate acoustic communications.

SUMMARY OF THE INVENTION

The present invention includes recognition of the problems and limitations of the prior art; and the need for secure communication systems of higher capacity/bandwidth less prone to interference. The invention provides a new and innovative method and apparatus for communications with greater accuracy and increased bandwidth over prior art methods. The communications method and apparatus described herein can be employed with acoustic communications and is therefore especially suitable for use in underwater communications such as, for example, between submerged vessels or undersea autonomous vehicles (UUVs). The communications method and apparatus described herein can additionally be employed in environments where electromagnetic communication via radio wave or light is not feasible, such as around sensitive equipment, in certain hospital settings, or in certain medical applications.

According to one aspect of the invention a method of acoustic communication includes creating helical waves of right-handed and left-handed helicity, wherein the helicity is modulated, or changed from left to right, to encode the message.

According to another aspect of the invention a circuit for encoding messages via right and left handed helicity is provided wherein the helicity of the signal can change without interrupting transmission of the signal.

According to yet another aspect of the invention, the helical encoding of information onto a pressure wave provides at least three layers of message security not found in the prior art. First, the screw-like rotation of the pressure wave itself makes it unlikely or difficult for prior art acoustic modems or detectors to accurately capture the signal. Second, the directionality (left/right) of the helical wave rotation used to encode information onto the signal requires special demodulation equipment and techniques. Third, the information to be encoded in the form of an acoustic helical wave can be encrypted or further modulated. That encrypted or modulated signal can then be converted to the form of an acoustic helical wave for an even greater level of security. The physical properties of the acoustic helical wave of the present invention also make interference and distortion less likely than in prior art communications systems.

According to still another aspect of the invention, the invention includes a communication system for transmitting and receiving messages acoustically via helical wave encoding.

Further advantages and features of the present invention will be described in detail below.

BRIEF DESCRIPTION OF THE DRAWINGS

Like reference numerals refer to similar elements or features throughout the drawings.

DESCRIPTION OF EXEMPLARARY EMBODIMENTS OF THE INVENTION

Figure 1:
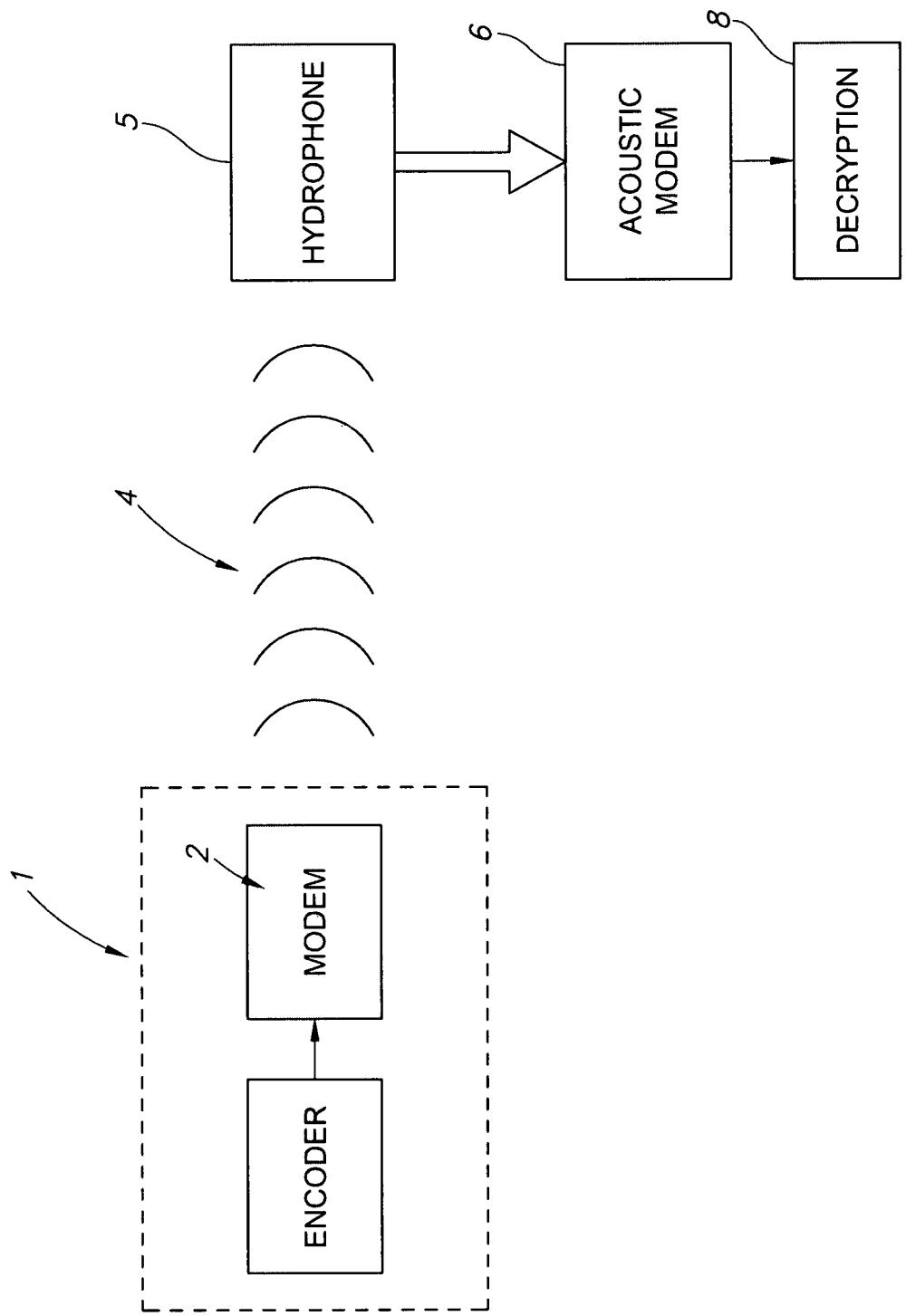
FIG. 1 is an illustration of a prior art acoustic communication system.
Figure 2B:
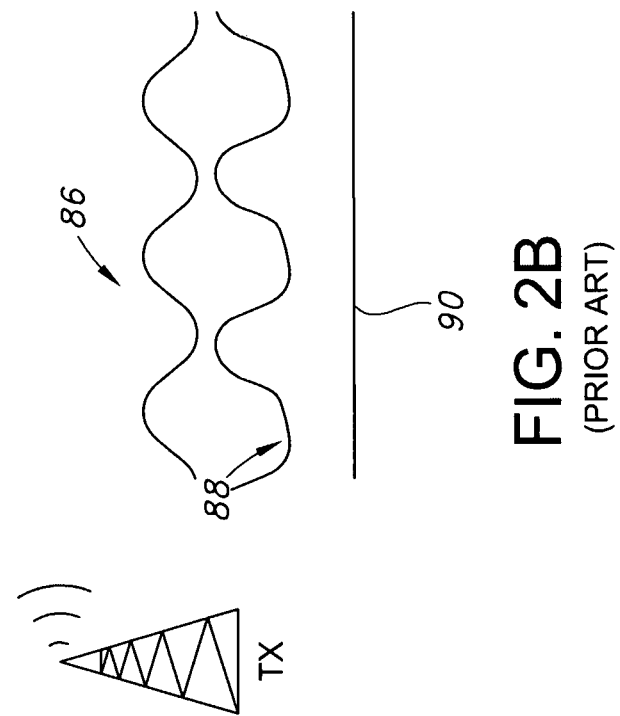
FIG. 2B is an illustration of an additional type of interference known to those of skill in the art.
Figure 2A:
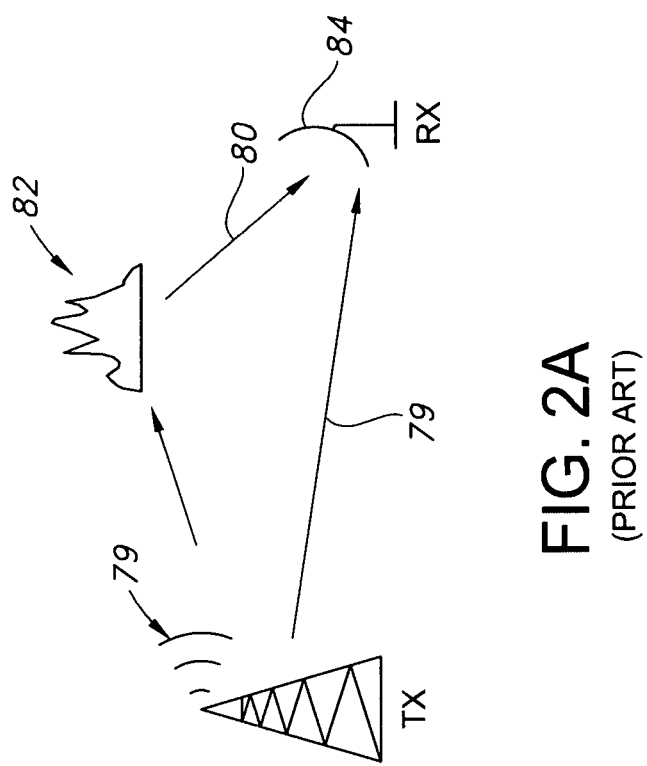
FIG. 2A is an illustration of one form of multipath interference known to those of skill in the art.
Figure 3B:
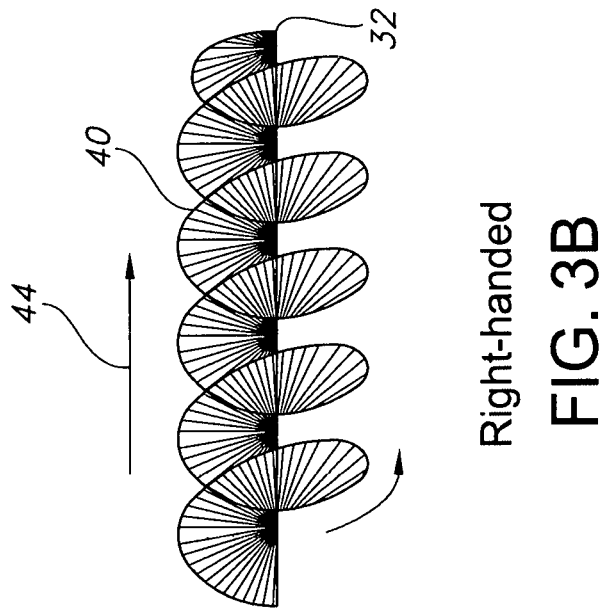
FIG. 3B illustrates a right-handed helical acoustic wave according to an embodiment of the invention.
Figure 3A:
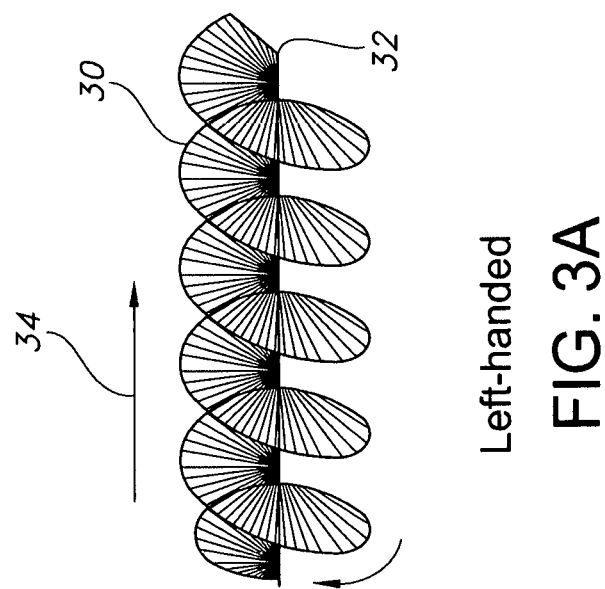
FIG. 3A illustrates a left-handed helical acoustic wave according to an embodiment of the invention.

According to one embodiment of the invention, information is transmitted via helical acoustic waves. FIGS. 3A and 3B illustrate helical acoustic waves of opposite helicities. The drawing of FIG. 3A, shows a first wave 30 which rotates counter-clockwise about an imaginary axis 32 as it propagates in the direction of arrow 34. Wave 30 is said to be 'left-handed,' or to have 'left-handed helicity.' The drawing of FIG. 3B shows a right-handed spiral wave 40 that rotates clockwise about imaginary axis 32 as it travels in the direction of arrow 44.

The creation and modulation of helical waves containing information according to embodiments of the invention are explained with reference to the circuit diagram of FIG. 4 and the waveform diagrams of FIGS. 5A and 5B. In operation, the circuit of FIG. 4 receives an input signal 100 which includes information to be transmitted acoustically. Input signal 100 may be in the form of an encoded message or encoded information, or may comprise other types of information carrying signals as in known to those of skill in the art.

Figure 4:
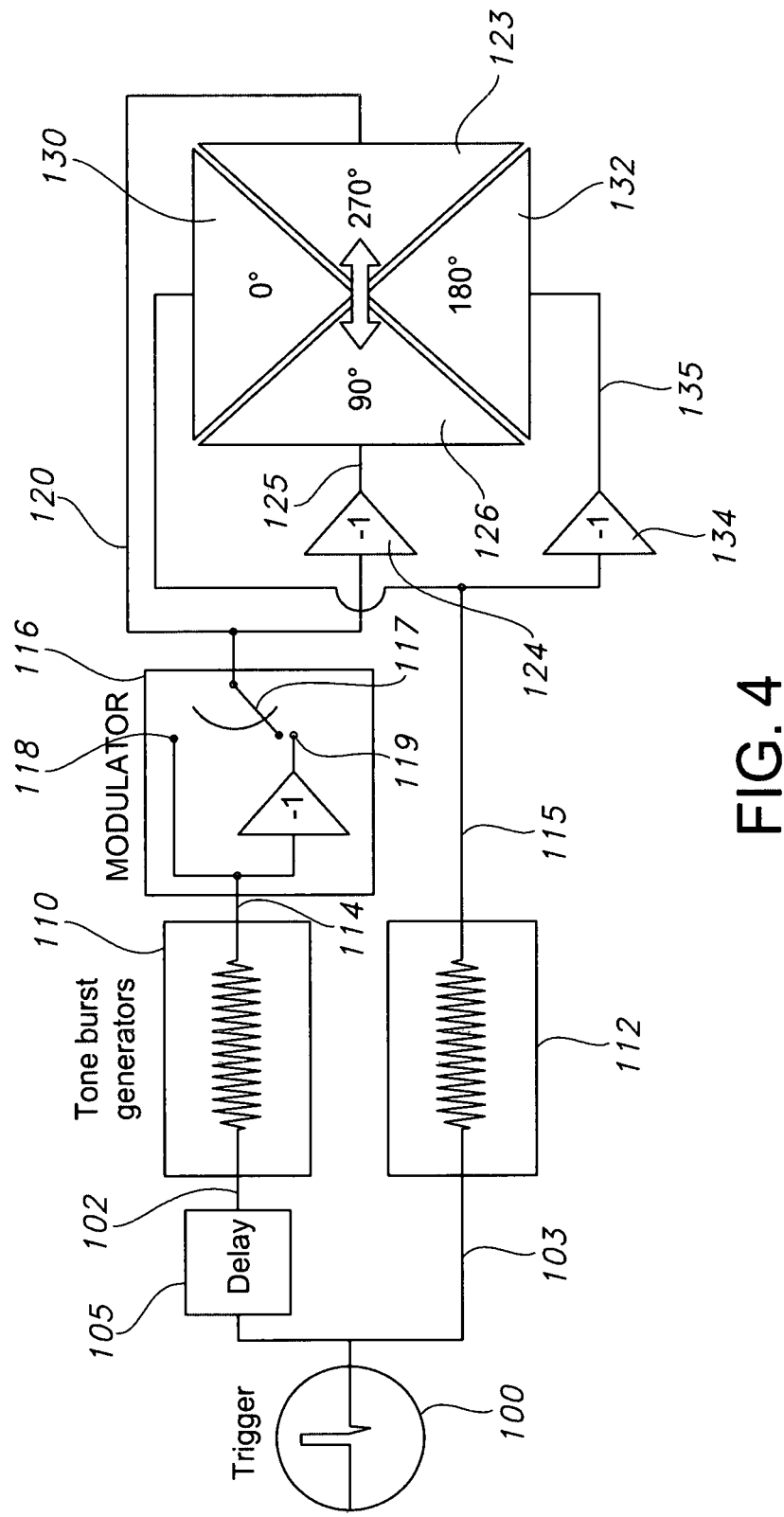
FIG. 4 diagrams a circuit for generating helical waves, according to an embodiment of the invention.
Figure 5A:
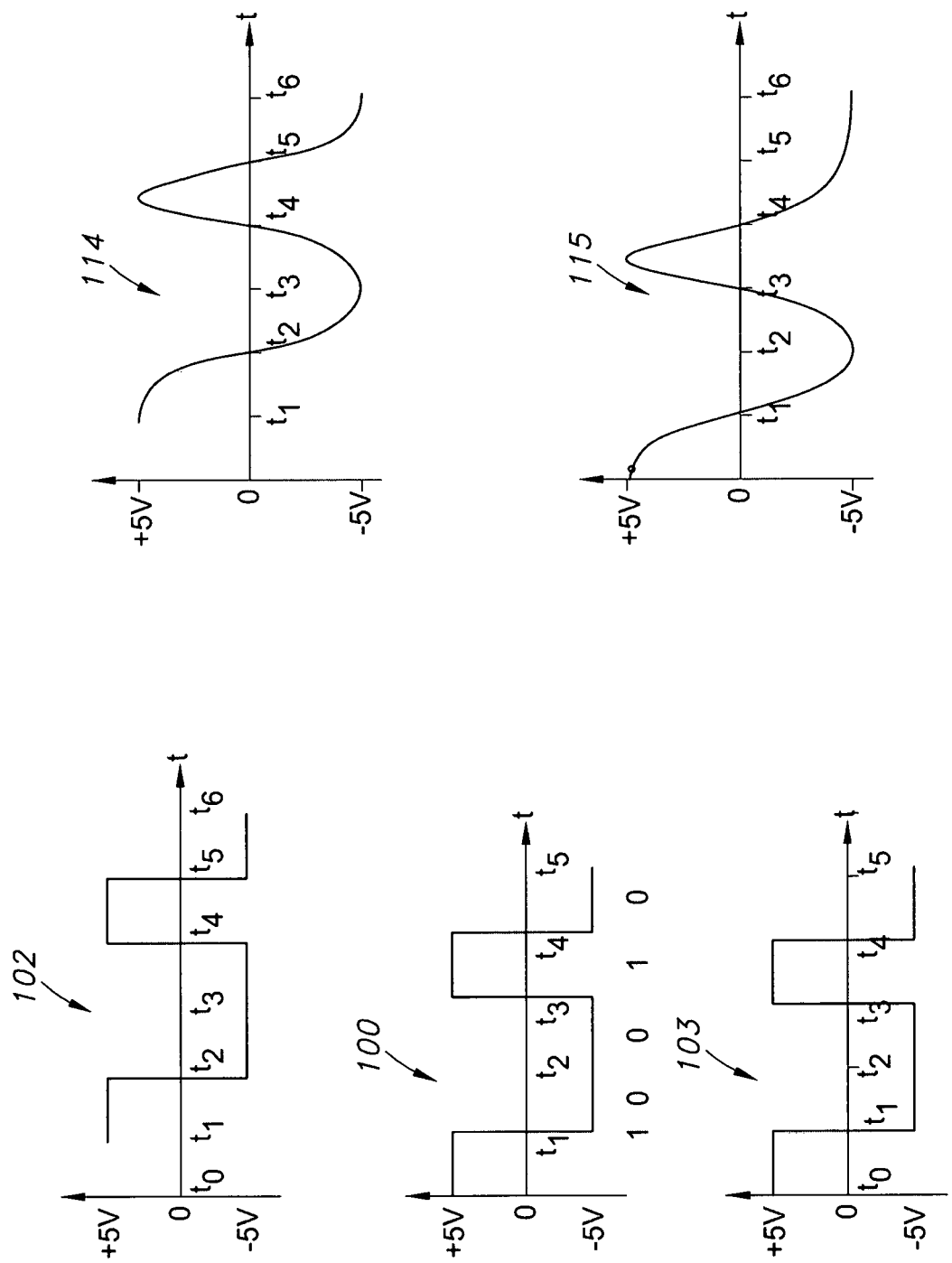
FIG. 5A and FIG. 5B show the waveforms of signals at various stages of the circuit of FIG. 4 according to an embodiment of the invention.
Figure 5B:
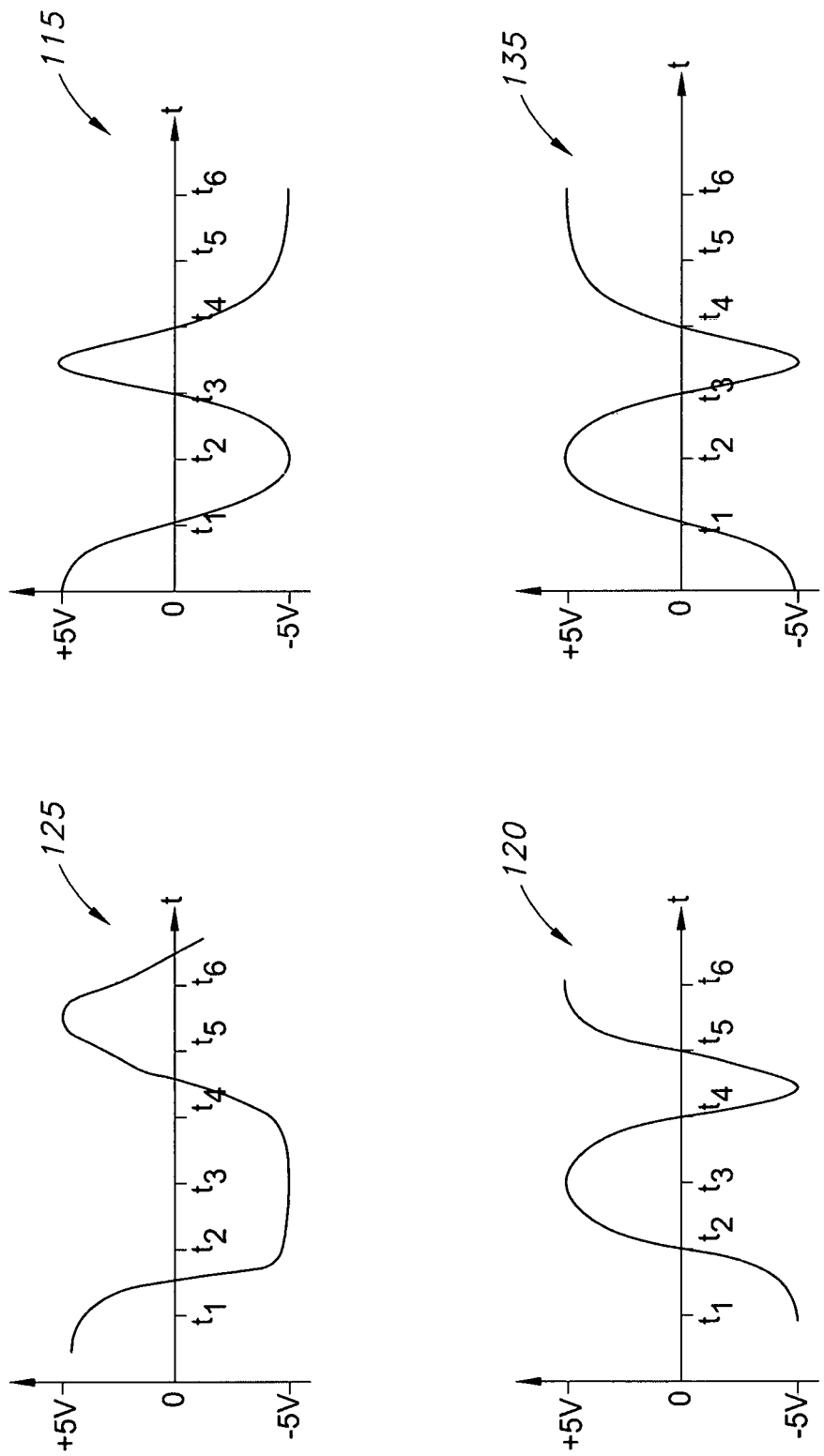

Solely as an example to illustrate operation of the circuit of FIG. 4, assume input signal 100 comprises a string of binary information having the sequence: 1001 as illustrated in FIG. 5A. In this illustrative example, a binary information value of 1 is represented as +5 volts for one millisecond of time; while a binary information value of 0, is represented by −5 volts for one millisecond of time. Other methods, voltages, and time durations for representing binary values and digitally encoding information are known to those of skill in the art and are equally suitable for use with the invention. Other, analogue means of encoding information into input signal 100 are also widely known to those of skill in the art and are also equally suitable for use with the invention. The input signal 100 waveform of FIG. 5A, however, serves as a simple example to illustrate operation of the invention.

Once received by the circuit of FIG. 4, input signal 100 is split into a delayed signal 102 and a non-delayed signal 103. Delayed signal 102 is delayed, or shifted in phase relative to non-delayed signal 103, by a delay 105. Delay 105 can be constructed according to a variety of techniques known to those of skill in the art. The article, "Delay Circuits," by Jose M. Quintana and Maria J. Avedillo in the *Wiley Encyclopedia of Electrical and Electronics Engineering,* also located online at: https://dpi.org/10.1002/047134608X.W229 and incorporated herein by reference describes numerous techniques and methods for constructing delay circuits. According to one embodiment of the invention, delay 105 slows delayed signal 102 in a range of 7 kHz to 15 kHz and delays its phasing by 90°.

In the operation example described herein, the resulting delayed signal 102 has the waveform shown in FIG. 5A. The waveform of non-delayed signal 103 is also shown in FIG. 5A. Comparing the waveform for delayed signal 102 with non-delayed signal 103 shows that the delayed signal 102 begins and ends later in time than signal 103 although the shape of the waveforms remains the same.

As shown in FIG. 4, each of delayed signal 102 and non-delayed signal 103 then passes through a tone burst generator 110 and 112 respectively. Tone burst generators 110 and 112 each generate a sine wave of a given frequency. The sine wave frequency of tone burst generators 110 and 112 determine the frequency of the resulting spiral wave. The frequency chosen for tone burst generators 110 and 112 can be any frequency but are usually selected based on the range and bandwidth of communication desired. Lower frequencies have longer range while higher frequencies can carry more information per unit of time.

The digital waveforms 102 and 103, when added to the sine wave generated by tone burst generators 110 and 112, convert the information encoded in digital waveforms 102 and 103, to a sinusoidal waveform 114 and 115 containing the same information. The resulting waveforms 114 and 115 are shown in FIG. 5A. In the example as illustrated in FIG. 5A, waveforms 114 and 115 also represent a binary value of 1 as +5 volts and a binary value of o as (−)5 volts, but as a sinusoidal waveform rather than as a digital waveform. Other sine wave frequencies and voltage values are possible as is well known to those of skill in the art.

In the circuit embodiment of FIG. 4, signal 114 is fed into a modulator 116. Modulator 116 determines how the helical wave is modulated: i.e. whether a right handed spiral or left handed helical corresponds to a binary 1. In the circuit of FIG. 4, modulator 116 includes a switch 117 that selects between a first signal path 118 which does not alter signal 114; and a second signal path 119 which inverts signal 114. Inverting signal 114 in this manner to obtain waveform 120 is also known as phase shifting signal 114 by 180 degrees. The resulting waveform is shown in FIG. 5B. When switch 117 of modulator 116 is set to select signal 120, the output of the circuit of FIG. 4 will produce a right handed helical wave whenever input signal 100 contains a binary 1 and a left handed helical wave whenever input signal 100 contains a binary zero. If switch 117 were positioned to select signal 118 instead, the opposite would occur: the circuit of FIG. 4 would output a left handed helical wave whenever input signal 100 contained a binary 1 and a right handed helical wave whenever input signal 100 contained a binary zero. In the circuit of FIG. 4 as drawn, the circuit will output a right handed spiral wave whenever input signal 100 indicates a binary 1 and a left handed spiral wave whenever input signal 100 indicates a binary zero.

Thus the helicity of the wave changes continuously and automatically as a function of the data input signal. The transmission of the helical wave is not interrupted or stopped. In addition, the position of switch 117 can also be reset electronically and without having to stop or interrupt transmission. The ability to electronically change how the helicity of the helical wave modulates the information while still transmitting allows for a greater amount of wave shapes to be created for encoding thereby adding greater security to transmitted messages. The ability to dynamically vary the modulation also enables a variety of compression schemes for data which further increases the information content of transmitted messages.

Switch 117 can be set manually to select between signal paths 120 and 118 prior to input of signal 100. Optionally, modulator 116 can be coupled to a clock or master keying mechanism 121 that automatically selects the position of switch 117 according to a predetermined or stored scheme.

In the example as shown in FIG. 4, signal 120 from modulator 116 is provided as input to transducer 123. Signal 120 is also supplied to inverter 124 which outputs a signal 125 supplied to transducer 126. Output 115 from tone burst generator 112 is provided to transducer 130. Signal 115 is also inverted by inverter 134 which outputs a signal 135 before being supplied to transducer 132. FIG. 5B illustrates each of waveforms 120, 125, 115 and 135 that are supplied to the transducers.

Transducers 123, 126, 130 and 132 each comprise a transducer constructed according to the teachings of U.S. Pat. No. 8,638,640 and incorporated herein by reference. Transducers vibrate in response to electrical signals and that vibratory motion converts the electrical signal into an acoustic pressure wave. Signals 120, 125, 115 and 135 move the individual transducers 126,123, 130 and 132 to form acoustic spiral waves. In response to the sinusoidal motion of the waveforms, transducers 126, 123, 130 and 132 move either forwards or backwards. This forward and backward movement of the transducer as the waveform goes up and down, converts the electrical sinusoidal signals into the physical vibrations that form the acoustic wave.

Each of transducers 123 and 126 is 90° out of phase with the two adjoining transducers 130 and 132, creating a pair of perpendicular acoustic dipoles. According to one embodiment of the invention, each opposing pair of transducers, i.e. 123 and 126; and 130 and 132, is 180° out of phase with its opposite partnering transducer. The pulses of the sine waves of the delayed and non-delayed signals through transducers 123, 126, 130 and 132 combined with the phase shifting caused by phase modulator 116, creates the spiral/helical shape of the acoustic wave.

With switch 117 set to select signal 120, transducer 130 will push forward, followed by a second transducer 126; this second transducer being 90° out of phase with the first. A third transducer 132, being opposite the first transducer in position and 180° out of phase with transducer 130, will move in the opposite direction, pulling away slightly. The fourth transducer 123, being 90° out of phase with transducer 132, will also pull away shortly after. The resulting helical wave will twist to the right, whenever input signal 100 indicates a binary 1. In this illustrative example, whenever input signal 100 contains a binary zero, the portion of the waveform of signals that correspond to that binary information, causes the phasing of transducers 126 and 123 to switch, and transducer 123 to be 90° out of phase with transducer 130, producing a left handed helical wave.

The helical wave output from the circuit of FIG. 4 is directional. Unlike a conventional sound wave which moves outward from the transmitter like a thrown rock rippling on a pond, the helical wave moves primarily along a line substantially orientated at the receiver. This property assists in making the helical wave a secure means of transmission. The helical wave is difficult to detect by another receiver not in the direct line of the wave and any receiving or detection device located outside the physical boundaries of the helical wave will not be able to separate any of the acoustics of the helical wave from the ambient acoustic noise of the environment.

Figure 6:
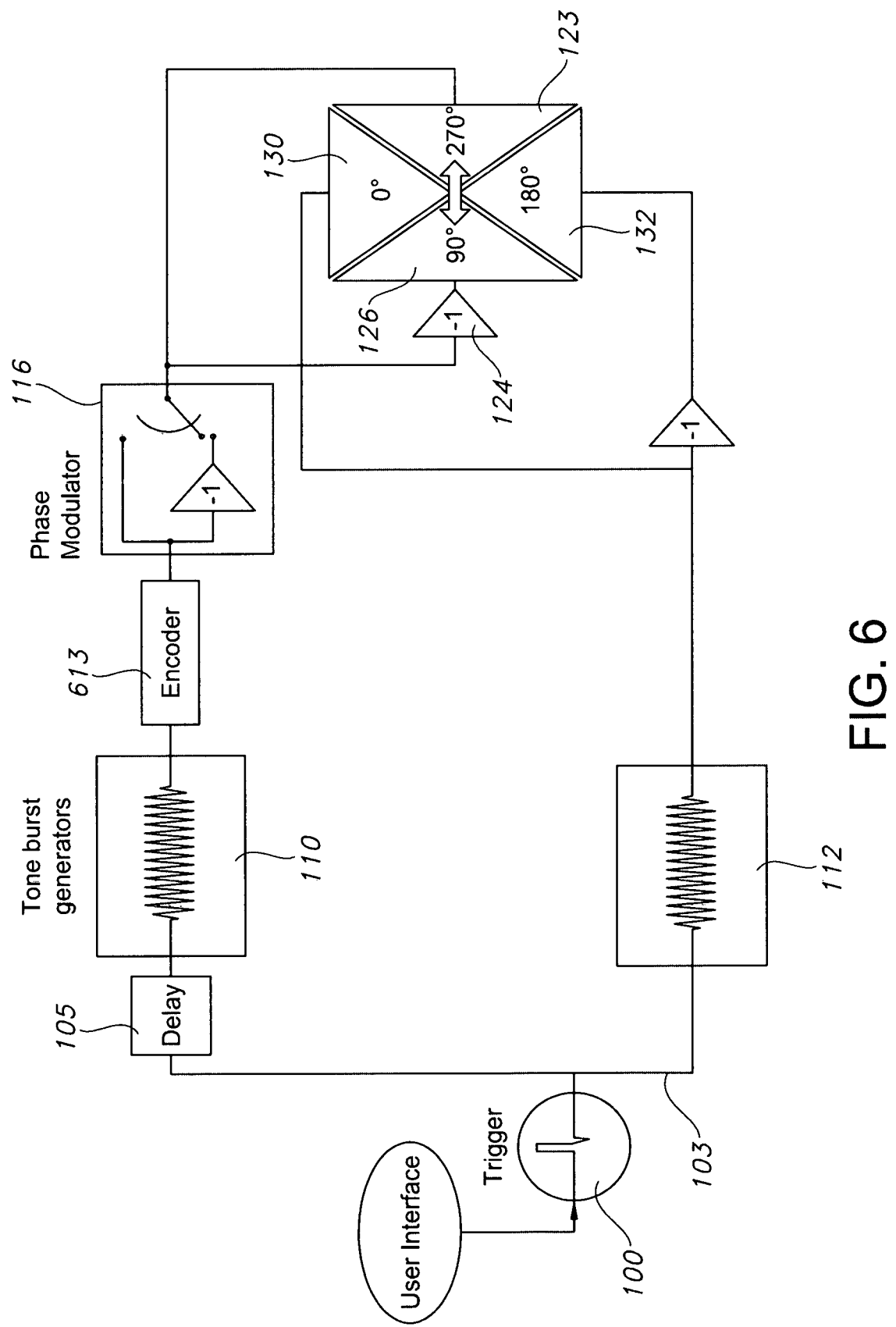
FIG. 6 diagrams a circuit for encrypting and transmitting information via helical wave according to an alternative embodiment of the invention.

FIG. 6 illustrates an alternative embodiment of the invention further including an encoder 613 for encrypting the information contained in signal 100. In operation, the circuit of FIG. 6 functions in a manner similar to the circuit of FIG. 4, except that now the information to be transmitted has been encrypted by encoder 613. In the embodiment of FIG. 6, encoder 613 is located after tone burst generator 110 and encrypts the output of tone generator 110. Alternatively, encoder 613 may be located before tone burst generator no, to encrypt the signal while it is still in digital, not analog form.

Figure 7:
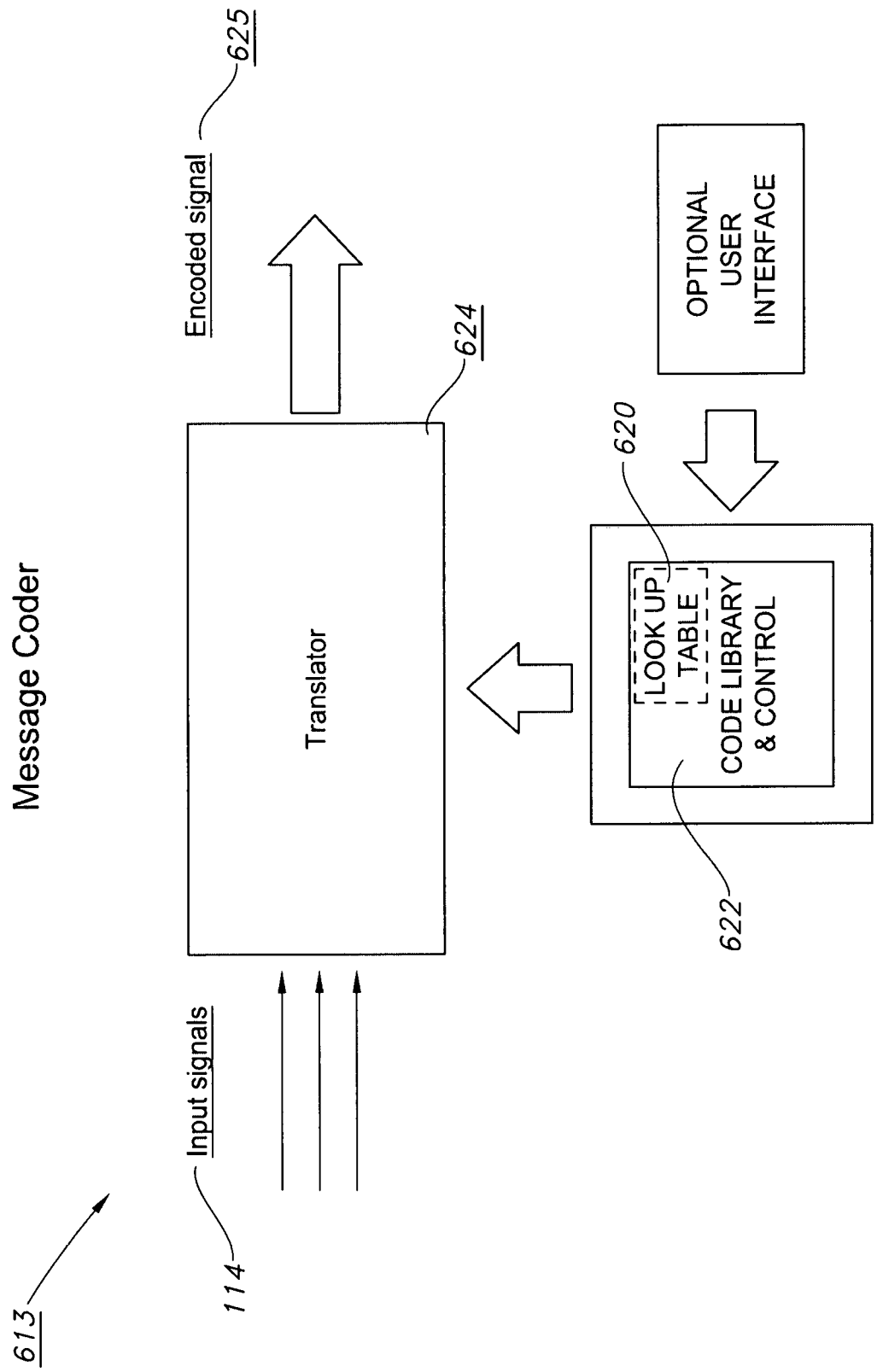
FIG. 7 is a block diagram of a message coder according to an embodiment of the invention

FIG. 7 describes the operation of encoder 613 in greater detail. The sine waves 114 output from tone generators 110 are input to encoder 613. Encoder 613 applies an algorithm that encrypts a cipher to the sine waves, encoding the delayed signal 102. The input to encoder 613 is checked against a look up table 620 that is included within a code library 622. Look up table 620 stores information that assigns an encryption to the information represented by signal 114 according to the code library 622. Translator 624 then applies the encryption to signal 114 according to the encryption data supplied by look up table 620 to create encoded message 625. A portion of the algorithm's encoding can optionally contain information added to the waveform 114 that determines which position phase modulator 116 will be in for which part of delayed signal. An optional user interface may also be included to select the upload encryption keys, modify the contents of the look up table 620 or select encryption to be used.

In prior art, phase modulator 116 had to be switched manually, meaning transmission of a message had to stop in order to change the helicity of the helical wave. In the current invention, the switch in phase modulator 116 is moved electronically, via the encoded modulation from encoder 613. Code library 622, and its associated control in encoder 613, and code library 622 may include a proprietary or confidential set of code to be determined by the user of the invention. This helps to secure the communication and transmission of data.

Figure 8:
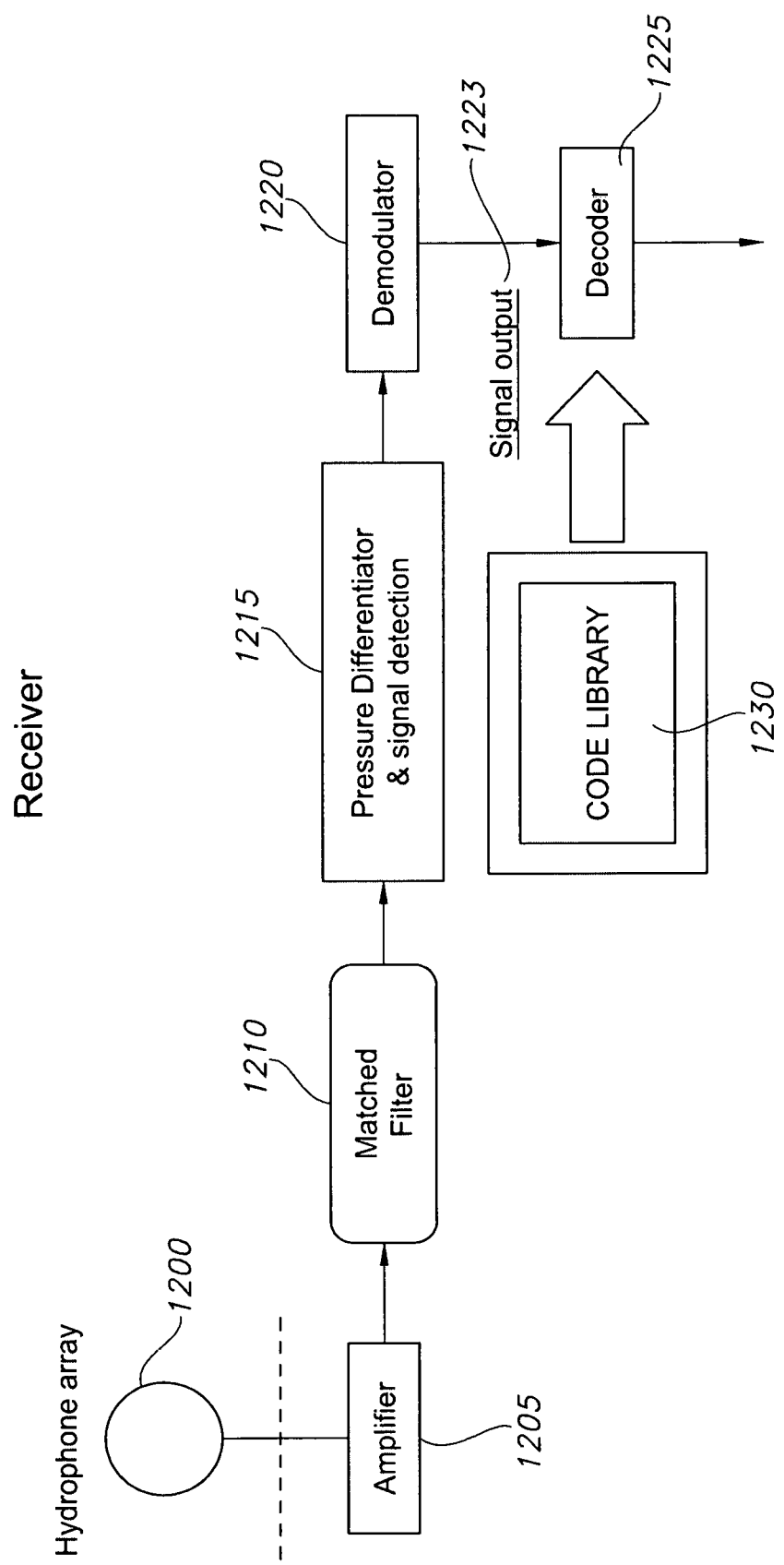
FIG. 8 shows a receiver system that is useful to capture and decode the helical wave, according to an embodiment of the invention.

FIG. 8 is a circuit useful in receiving spiral acoustic waves. Hydrophone array 1200 detects the sounds from the surrounding sound field as pressure waves. A pressure wave transmitted to a piezo-electric hydrophone causes the piezo-electric material to contract, creating an electric signal. This electric signal is transmitted to amplifier 1205, to strengthen the signal. The signal travels through matched filter 1210 that filters out background noise from the transmitted acoustic signal. The filtered signal is then input to pressure differentiator and signal detector 1215. Pressure differentiator and signal detector 1215 use the pressure derivative of, to calculate the pressure gradient that matches the pressure of the modulated helical wave, finding the real signal waves from the output of matched filter 1210. This is the encoded spiral wave. The encoded helical wave continues to demodulator 1220, where the phasing of the helical wave is reversed. The signal output 1223 is the demodulated helical wave. Signal output 1223 moves to decoder 1225. Decoder 1225 first translates signal output 1223 from an electrical signal to binary. This binary is then cross-referenced with the look-up table in code library 1230 to decipher the encoded message. Code library 1230 is housed in decoder 1225. Once decoded, the message is forwarded to the user interface.

Should another receiver pick up the acoustics of the helical wave, without the cipher embedded in decoder 1225, the transmission is useless. The correct receiver has a decoder with the appropriate cipher included in its coding that will decode the message. The receiver's hydrophone array 1200, consisting of a plurality of piezo-electric hydrophones, will detect the pressures of the helical wave. As the helical wave hits hydrophone array 1200, the piezo-electric material in the hydrophones compresses accordingly to the amount of pressure from the helical wave. This compression is converted to an electrical signal that is sent to amplifier 1205. The signal's strength is increased in amplifier 1205 before it is sent to matched filter 1210.

Matched filter 1210 compares the amplified sound signals against a set of known signal waves for possible matches. In this example, match filter 1210 finds signal waves similar to the inverted encoded sine waves generated by 1-0-0-1-0. The matches are sent to the pressure differentiator and signal detection 1215. Here, the original algorithm and its derivative, referred to as a pressure derivative, are used to calculate each matched signal. Pressure differentiator 1215 measures the difference of pressures at different points on the helical wave as they made contact with hydrophone array 1200.

The difference in pressures is divided by the distance between the hydrophones. The quotient calculated returns a positive or negative number which is related to the $\mu$ variable in the derivative and in the original algorithm. This is used by signal detection 1215 to detect the true signal of 0-1-1-0-1: the inverted encoded sine wave carrying 1-0-0-1-0. Pressure differentiator and signal detection 1215 also identifies which parts of the encoded message have their phasing modulated.

The encoded message now moves to demodulator 1220. Any part of the message that had its phasing modulated will now be reverted back. In the example, 1-0-0-1-0 was modulated from 90° to 270° to 90°. Demodulator 1220 will return it to the original 90°. The now reverted encoded electronic message continues to decoder 1225.

Decoder 225 first converts the electronic message to binary, and then it will decode the binary message. Housed within decoder 1225 is another copy of the code library, code library 1230. As before, code library 1230 is a look up table. It also proprietary or confidential to the enterprise. The exact way in which the message is decoded will also be proprietary or confidential to the enterprise, same as the encoding process. In this example, for encoding all 1's were converted to 0's, and all 0's were converted to 1's. After converting the electronic message to a binary one, decoder 1225 will reverse this conversion, so that 0-1-1-0-1 will return to the original message of 1-0-0-1-0. The binary message has now been decoded and is pushed to the user interface.

The subject matter defined in the appended claims is not necessarily limited to the specific features or acts described above. Rather, the specific features and acts are disclosed as example forms of implementing the claims. Many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A circuit for generating acoustic helical waves, comprising:
   an input for receiving an information signal;
   a first and second tone burst generators coupled to said input, the first and second tone burst generators adapted to receive said information signal and to output a first and a second analogue signal respectively;
   a delay circuit disposed between said first tone burst generator and said input, the delay circuit adapted to phase shift said information signal prior to receipt of said information signal at said first tone burst generator;
   a modulator coupled to said first tone burst generator, said modulator comprising
   a switch selectable between a first position and a second position,
   wherein said modulator phase shifts said first analogue signal when said switch is in a first position, and wherein a phase of said first analogue signal remains unaltered when said switch is in a second position; and, four transducers for converting said first and second analogue signals to a plurality of acoustic signals, the four transducers comprising a first transducer, a second transducer, a third transducer, and a fourth transducer, the first transducer coupled to receive said second analogue signal from said second tone burst generator, wherein said first transducer has a first phase the second transducer coupled to said second tone burst generator and to a first inverter for receiving an inverted second analogue signal, wherein said second transducer is 180 degrees out of phase with said first transducer, the third transducer coupled to an output of said modulator for receiving said first analogue signal, wherein said third transducer is 270 degrees out of phase with said first transducer, the fourth transducer coupled to an output of said modulator and to a second inverter for inverting an output of said modulator, wherein said fourth transducer is 90 degrees out of phase with said first transducer.

2. The circuit of claim 1, further comprising:
a message coder coupled to the modulator for selecting between the first and said second position of the switch.

3. The circuit of claim 2, further comprising:
a message library coupled to said message coder.

4. A method for encoding electronic information as helical acoustic waves via the circuit of claim 1, comprising the steps of:
receiving an electronic information signal, the electronic information signal comprising the information signal;
representing said electrical information signal as the first and second analogue signals;
supplying said first analogue signal to the first transducer having the first phase and the second transducer having the second phase;
supplying said second analogue signal to the third transducer having the third phase and the fourth transducer having the fourth phase;
outputting said first analogue signal as a first and second acoustic signal at said first and second transducer respectively; and,
outputting said second analogue signal as a third and fourth acoustic signal at said third and fourth transducer respectively, wherein the plurality of acoustic signals comprise the first, second, third and fourth acoustic signals.

5. The method of claim 4, wherein said step of receiving an electrical information signal comprises the step of receiving a digital signal.

6. The method of claim 4, wherein said step of receiving an electrical information signal comprises the step of receiving a sinusoidal signal.

7. The method of claim 4, further comprising the step of:
encrypting at least one of said first and said second analogue signals.

8. The method of claim 4, wherein the circuit comprises a medical device, said steps of outputting a first and a second analogue signal further comprises the steps of outputting said first, said second, said third, and said fourth acoustic signals in a medical application.

9. The method of claim 8, wherein said steps of outputting said first, said second, said third, and said fourth acoustic signals in the medical application further includes the step of transmitting said acoustic signals through a bodily fluid.

10. The method of claim 8, wherein said steps of outputting said first, said second, said third, and said fourth acoustic signals in the medical application further includes the step of transmitting said acoustic signals through a bodily tissue.

* * * * *